United States Patent [19]
Commons et al.

[11] Patent Number: 6,034,272
[45] Date of Patent: Mar. 7, 2000

[54] ELEVATION OF HDL CHOLESTEROL BY N-[4-[(AMINOTHIOXOMETHYL) HYDRAZONO]-4-ARYLBUTYL]AMIDES

[75] Inventors: Thomas Joseph Commons, Wayne; Susan Christman, Philadelphia, both of Pa.

[73] Assignee: American Home Products Corporation, Madison, N.J.

[21] Appl. No.: 09/096,223

[22] Filed: Jun. 11, 1998

Related U.S. Application Data

[60] Provisional application No. 60/049,699, Jun. 16, 1997.

[51] Int. Cl.$^7$ .................................................. C07C 337/00
[52] U.S. Cl. .................. 564/19; 564/20; 560/23; 560/30
[58] Field of Search .......................... 560/23, 30; 564/19, 564/20

[56] References Cited

U.S. PATENT DOCUMENTS 4,983,755  1/1991  Bühmann et al. .......................... 560/24

FOREIGN PATENT DOCUMENTS 03024009  2/1991  Japan .
07149706  6/1995  Japan .

OTHER PUBLICATIONS

Russ et al., *Am. J. Med.*, 11:480–493 (1951).
Gofman et al., *Circulation*, 34:679–697 (1966).
Miller and Miller, *Lancet*, 1:16–19 (1975).
Gordon et al., *Circulation*, 79:8–15 (1989).
Stampfer et al., *N. England J. Med.*, 325:373–381 (1991).
Badimon et al., *Lab. Invest. .*, 60:455–461 (1989).
Miller et al., *Br. Med. J.*, 282:1741–1744 (1981).
Picardo et al., *Arteriosclerosis.*, 6:434–441 (1986).
Glomset, *J. Lipid Res.*, 9:155–167 (1968).
Glass et al., *Circulation*, vol. 66, Suppl. II 102 (1982).
MacKinnon et al., *J. Biol. Chem.*, 261:2548–2552 (1986).
Grow and Fried, *J. Biol. Chem.*, 253:8034–8041 (1978).
Lagocki and Scanu, *J. Biol. Chem.*, 255:3701–3706 (1978).
Schaefer et al., *J. Lipid Res. .*, 23:1259–1273 (1982).
Tomita et al., *J. Heterocyclic Chem.*, 27:707–710 (1990).
Vega and Grundy, *Current Opinion in Lipidology*, 7:209–216 (1996).

Primary Examiner—Gary L. Kunz
Assistant Examiner—Everett White
Attorney, Agent, or Firm—Michael R. Nagy

[57] ABSTRACT

This invention relates to the treatment of atherosclerosis via raising the level of HDL cholesterol by administration of a compound of the formula

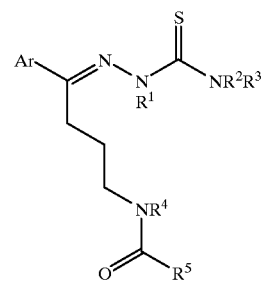

wherein:

$R^1$, $R^2$, and $R^3$ are independently hydrogen, $C_1-C_6$ alkyl or —$(CH_2)_{0-6}$Ph where Ph is phenyl is optionally substituted by halogen, cyano, nitro, $C_1-C_6$ alkyl, $C_1-C_6$ alkoxy, trifluoromethyl, $C_1-C_6$ alkoxycarbonyl, —$CO_2H$ or OH;

$R^4$ is hydrogen or $C_1-C_6$ alkyl;

$R^5$ is hydrogen, $C_1-C_6$ alkyl, $C_3-C_8$ cycloalkyl, or —$(CH_2)_{0-6}Ar^1$ where $Ar^1$ is phenyl, naphthyl, furanyl, pyridinyl or thienyl and $Ar^1$ can be optionally substituted by halogen, cyano, nitro, $C_1-C_6$ alkyl, phenyl, $C_1-C_6$ alkoxy, phenoxy, trifluoromethyl, $C_1-C_6$ alkoxycarbonyl, —$CO_2H$ or OH; and Ar is phenyl, naphthyl, furanyl, pyridinyl or thienyl or Ar is optionally substituted by halogen, cyano, nitro, $C_1-C_6$ alkyl, phenyl, $C_1-C_6$ alkoxy, phenoxy, tifluoromethyl, $C_1-C_6$ alkoxycarbonyl, —$CO_2H$ or OH.

21 Claims, No Drawings

ELEVATION OF HDL CHOLESTEROL BY N-[4-[(AMINOTHIOXOMETHYL) HYDRAZONO]-4-ARYLBUTYL]AMIDES

This application claims benefit of priority to provisional patent application number 60/049,699 filed on Jun. 16, 1997.

FIELD OF INVENTION

This invention relates to compounds useful in elevating high density lipoprotein, the "good" cholesterol. Compounds of this invention increase plasma levels of HDL in a cholesterol fed rat model and as such these compounds may be useful for treating diseases such as atherosclerosis.

BACKGROUND OF THE INVENTION

It is widely believed that HDL is a "protective" lipoprotein [Gloria Lena Vega and Scott Grundy, Current Opinion in Lipidology, 7, 209–216 (1996)] and that increasing plasma levels of HDL may offer a direct protection against the development of atherosclerosis. Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.*, 11 (1951) 480–493; Gofman et al, *Circulation*, 34 (1966) 679–697; Miller and Miller, *Lancet*, 1 (1975) 16–19; Gordon et al., *Circulation*, 79(1989) 8–15; Stampfer et al., *N. Engl. J. Med.*, 325(1991) 373–381; Badimon et al., *Lab. Invest.*, 60(1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles in humans appears to be correlated to a decreased number of sites of stenosis in the coronary arteries of humans (Miller et al., *Br. Med. J.*, 282 (1981) 1741–1744).

There are several mechanisms by which HDL may protect against the progression of atherosclerosis. Studies in vitro have shown that HDL is capable of removing cholesterol from cells (Picardo et al., *Arteriosclerosis*, 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.*, 9 (1968) 155–167). This has been supported by experiments showing efficient transfer of cholesterol from HDL to the liver (Glass et al., *Circulation*, 66 (Suppl. II) (1982) 102; MacKinnon et al., *J. Biol. Chem.*, 261 (1986) 2548–2552). In addition, HDL may serve as a reservoir in the circulation for apoproteins necessary for the rapid metabolism of triglyceride-rich lipoproteins (Grow and Fried, *J. Biol. Chem.*, 253 (1978) 1834–1841; Lagocki and Scanu, *J. Biol. Chem.*, 255 (1980) 3701–3706; Schaefer et al., *J. Lipid Res.*, 23 (1982) 1259–1273). Accordingly, agents which increase HDL cholesterol concentrations are useful as anti-atherosclerotic agents, particularly in the treatment of dyslipoproteinemias and coronary heart disease.

BRIEF DESCRIPTION OF THE INVENTION

The compounds of this invention which elevate plasma levels of HDL cholesterol have the general structure

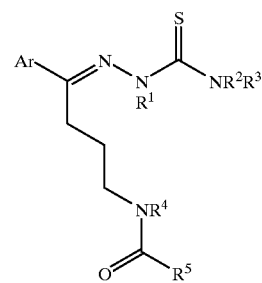

wherein:

$R^1$, $R^2$, and $R^3$ are independently hydrogen, $C_1$–$C_6$ alkyl or —$(CH_2)_{0-6}$Ph where Ph is phenyl is optionally substituted by halogen, cyano, nitro, $C_1$–$C_6$ alkyl $C_1$–$C_6$ alkoxy, trifluoromethyl, $C_1$–$C_6$ alkoxycarbonyl, —$CO_2H$ or OH;

$R^4$ is hydrogen or $C_1$–$C_6$ alkyl;

$R^5$ is hydrogen, $C_1$–$C_6$ alkyl, $C_3$–$C_8$ cycloalkyl, or —$(CH_2)_{0-6}Ar^1$ where $Ar^1$ is phenyl, naphthyl, furanyl, pyridinyl or thienyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl, naphthyl, furanyl, pyridinyl or thienyl or Ar is optionally substituted by halogen, cyano, nitro, $C_1$–$C_6$ alkyl, phenyl, $C_1$–$C_6$ alkoxy, phenoxy, tifluoromethyl, $C_1$–$C_6$ alkoxycarbonyl, —$CO_2H$ or OH.

The compounds are tested in vivo in rats fed cholesterol-augmented rodent chow for 8 days according to the test protocol and blood from the rats analyzed for HDL cholesterol.

DETAILED DESCRIPTION OF THE INVENTION

The compounds of this invention are conveniently prepared by the route shown in Scheme I. Specific examples are given in the Experimental Section. These examples are for illustrative purposes only and are not to be construed as limiting to this disclosure in any way. Those skilled in the art will be aware of other methods of preparing compounds of this invention. The starting materials or intermediates are available commercially or can be prepared by standard literature procedures.

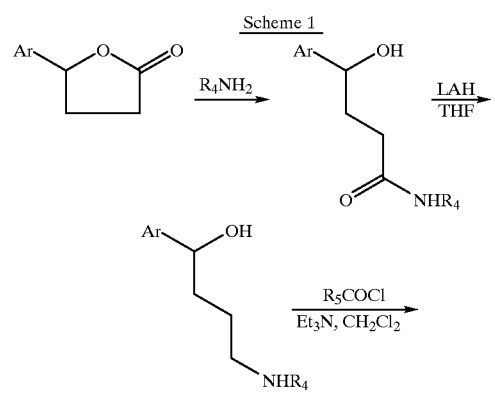

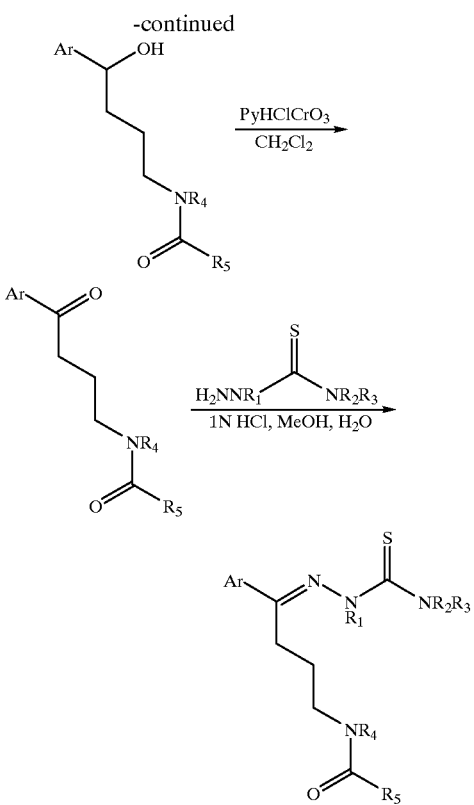

EXPERIMENTAL

Example 1

N-[4-[(Aminothioxomethyl)hydrazono]-4-phenylbutyl]-N-(1-methylethyl)acetamide (a) A mixture of γ-phenyl-γ-butyrolactone (10.0 g, 61.7 mmol) and isopropylamine (50 ml, 587 mmol) was stirred at room temperature for approximately 26 hours. The solvent was removed under reduced pressure to give 4-hydroxy-N-isopropyl-4-phenyl-butyramide (13.71 g, 100%) as a yellow solid, mp 131–135° C.

Elemental Analysis for $C_{13}H_{19}NO_2$ Calc'd: C, 70.56; H, 8.65; N, 6.33 Found: C, 70.24; H, 8.73; N, 6.24

(b) A solution of 4hydroxy-N-isopropyl-4-phenyl-butyramide (12.03 g, 54.4 mmol), prepared in the previous step, in 200 ml of anhydrous THF was added under nitrogen dropwise over 30 minutes to a suspension of LAH (5.18 g, 136 mmol) in 200 ml of anhydrous THF at room temperature. After the addition the reaction was refluxed for approximately 19 hours. After cooling to room temperature 5.18 ml of water was added dropwise followed by the dropwise addition of 5.18 ml of 15% KOH and 15.54 ml of water. After stirring at room temperature 30 minutes the solid was removed by filtration and the filtrate concentrated under reduced pressure to remove the THF. The residue was partitioned between methylene chloride and water. The organic layer was separated and the aqueous layer extracted three times with methylene chloride. The combined organic extracts were dried ($MgSO_4$) and the solvent removed under reduced pressure to give 10.22 g of a light yellow solid. The solid was dissolved in methylene chloride and extracted with 1 N HCl. The organic layer was separated and the aqueous layer extracted two times with methylene chloride. The aqueous layer was partitioned with methylene chloride and then made basic with 1 N NaOH. The organic layer was separated and the aqueous layer extracted five times with methylene chloride. The organic extracts were combined, dried ($MgSO_4$) and the solvent removed under reduced pressure to give 4-isopropylamino-1-phenyl-1-butan-1-ol (9.47 g, 84%) as a white solid, mp 61–67° C.

Elemental Analysis for $C_{13}H_{21}NO$ Calc'd: C, 75.32; H, 10.21; N, 6.76 Found: C, 75.26; H, 10.25; N, 6.52

(c) Acetyl chloride (4.47 ml, 62.9 mmol) in 200 ml of methylene chloride was added under nitrogen dropwise over 2 hours to a solution of 4-isopropylamino-1-phenyl-1-butan-1-ol (13.02 g, 62.8 mmol), prepared in the previous step, and triethylamine (8.75 ml, 62.8 mmol) in 250 ml of methylene chloride at ice bath temperature. After the addition the reaction was stirred at ice bath temperature for 2 hours. The ice bath was removed and the stirring continued for 20 hours (overnight). The reaction was extracted with 1 N HCl, dried ($MgSO_4$) and the solvent removed under reduced pressure to give N-(4-hydroxy-4-phenyl-butyl)-N-isopropyl-acetamide (16.29 g) as a yellow oil. The material was used in the following reaction without additional purification, MS [M+] m/e 249.

Elemental Analysis for $C_{15}H_{23}NO_2 \cdot 0.11CH_2Cl_2$ Calc'd: C, 70.15; H, 9.05; N, 5.41 Found: C, 69.92; H, 8.95; N, 5.32

(d) Pyridinium chlorochromate (20.35 g, 94.2 mmol) was added to a solution of N-(4-hydroxy-4-phenyl-butyl)-N-isopropyl-acetamide (15.69 g, 62.9 mmol), prepared in the previous step, in 350 ml of methylene chloride and the mixture stirred at room temperature for 2 hours. The entire reaction mixture was poured onto 750 g of silica gel (230–400 mesh) and the material eluted with 50% ethyl acetate-methylene chloride and then ethyl acetate. Isolation of the major fraction gave N-isopropyl-N-(4-oxo-4-phenyl-butyl)-acetamide (12.43 g, 80%) as a green solid, mp 36–39° C.

Elemental Analysis for $C_{15}H_{21}NO_2$ Calc'd: C, 72.84; H, 8.56; N, 5.66 Found: C, 73.11; H, 8.42; N, 5.60

(e) Thiosemicarbazide (6.1901 g, 67.9 mmol) was added to a solution of N-isopropyl-N-(4-oxo-4-phenyl-butyl)-acetamide (11.20 g, 45.3 mmol), prepared in the previous step, in 160 ml of methanol plus 12.2 ml of 1 N HCl, plus 12.2 ml of water and the reaction stirred at room temperature for 22 hours (overnight). The reaction was concentrated under reduced pressure to remove the methanol. The residue was partitioned between methylene chloride and water. The organic layer was separated, washed five times with water, dried ($MgSO_4$) and the solvent removed under reduced pressure to give 14.54 g of a yellow foam. The foam was crystallized from ethyl acetate to give 10.28 g (71%) of the title compound as a white solid, mp 141–147° C.

Elemental Analysis for $C_{16}H_{24}N_4OS$ Calc'd: C, 59.97; H, 7.55; N, 17.48 Found: C, 59.96; H, 7.46; N, 17.46

Example 2

N-[4-[(Aminothioxomethyl)hydrazono]-4-phenylbutyl]acetamide (a) A mixture of γ-phenyl-γ-butyrolactone (10.30 g, 63.5 mmol) and an excess of ammonia was stirred under nitrogen and a dry ice trap for 8 hours. The dry ice trap was removed and after evaporation of the ammonia 11.27 g of a tan solid remained. Recrystallization of this solid from ethyl acetate-hexane gave 4-hydroxy-4-phenyl-butyramide (8.56 g, 75%) as a white solid, mp 85–87° C.

Elemental Analysis for $C_{10}H_{13}NO_2$ Calc'd: C, 67.02; H, 7.31; N, 7.82 Found: C, 67.27; H, 7.25; N, 7.84

(b) A solution of 4-hydroxy-4-phenyl-butyramide (26.0 g, 0.145 mol), prepared in the previous step, in 400 ml of anhydrous THF was added under nitrogen dropwise over 1.5 hours to a suspension of LAH (11.0 g, 0.290 mol) in 300 ml of anhydrous THF at room temperature. After the addition the reaction was refluxed for approximately 21 hours. After cooling to room temperature 11 ml of water was added dropwise followed by the dropwise addition of 11 ml 15% KOH and 33 ml of water. After stirring at room temperature for 30 minutes the solid was removed by filtration and the filtrate concentrated under reduced pressure to remove the THF. The residue was partitioned between methylene chloride and water. The organic layer was separated and the aqueous layer extracted three times with methylene chloride. The combined organic extracts were dried ($MgSO_4$) and the solvent removed under reduced pressure to give 18.38 g of a waxy yellow solid. Recrystallization of the solid from ethyl acetate gave 4-amino-1-phenyl-butan-1-ol (4.95 g, 21%) as a white solid, mp 94–96° C.

Elemental Analysis for $C_{10}H_{15}NO$ Calc'd: C, 72.69; H, 9.15; N, 8.48 Found: C, 72.49; H, 9.04; N, 8.24

(c) Acetyl chloride (4.26 ml, 59.9 mmol) in 200 ml of methylene chloride was added under nitrogen dropwise over 3 hours to a solution of 4-amino-1-phenyl-butan-1-ol (9.90 g, 5.99 mmol), prepared in the previous step, and triethylamine (8.35 ml, 59.9 mmol) in 300 ml of methylene chloride at ice bath temperature. After the addition the reaction was stirred at ice bath temperature for 1 hour. The ice bath was removed and the stirring continued for 18 hours (overnight). The reaction was extracted with 1 N HCl, dried ($MgSO_4$) and the solvent removed under reduced pressure to give 9.04 g of a yellow oil. Purification of this oil on 700 g of silica gel (230–400 mesh) using ethyl acetate and then 1% to 5% methanol-ethyl acetate as the eluent gave N-(4-hydroxy-4-phenyl-butyl)-acetamide (6.30 g, 51%) as a light yellow oil, MS [M$^+$] m/e 207.

Elemental Analysis for $C_{12}H_{17}NO_2$.0.04 $CH_2Cl_2$.0.06 $C_4H_8O_2$ Calc'd: C, 68.30; H, 8.20; N, 6.49 Found: C, 66.98; H, 8.32; N, 6.27

(d) Pyridinium chlorochromate (10.08 g, 46.8 mmol) was added to a solution of N-(4-hydroxy-4-phenyl-butyl)-acetamide (6.46 g, 31.2 mmol), prepared in the previous step, in 200 ml of methylene chloride and the mixture stirred at room temperature for 1.5 hours. The entire reaction mixture was poured onto 200 g of silica gel (230–400 mesh) and the material eluted with ethyl acetate. Isolation of the major fraction gave N-(4-oxo-4-phenyl-butyl)-acetamide (4.35 g, 68%) as a light brown solid, mp 92–95° C.

Elemental Analysis for $C_{12}H_{15}NO_2$ Calc'd: C, 70.22; H, 7.37; N, 6.82 Found: C, 69.70; H, 7.38; N, 6.75

(e) Thiosemicarbazide (2.85 g, 31.3 mmol) was added to a solution of N-(4-oxo-4-phenyl-butyl)-acetamide (4.28 g, 20.9 mmol), prepared in the previous step, in 75 ml of methanol plus 5.6 ml of 1 N HCl, plus 5.6 ml of water and the reaction stirred at room temperature for 42 hours. The reaction was concentrated under reduced pressure to remove the methanol. The residue was partitioned between methylene chloride and water. The organic layer was separated, washed five times with water, dried ($MgSO_4$) and the solvent removed under reduced pressure to give 4.77 g of a yellow solid Recrystallization of this solid from ethyl acetate gave the title compound (3.53 g, 61%) as an off-white solid, mp 74–83° C.

Elemental Analysis for $C_{13}H_{18}N_4OS$.0.79 $C_4H_8O_2$ Calc'd: C, 55.78; H, 7.04; N, 16.10 Found: C, 55.72, H, 6.90; N, 15.97

Example 3

N-[4-[(Aminothioxomethyl)hydrazono]-4-phenylbutyl]-N-(1-methylethyl)benzamide

In the manner as described in Example 1 and substituting benzoyl chloride for acetyl chloride in step c, the title compound was obtained (3.75 g, 75%) as an off-white solid, mp 107–109° C.

Elemental Analysis for $C_{21}H_{26}N_4OS$.0.25 $C_4O_8O_2$ Calc'd: C, 65.32; H, 6.98; N, 13.85 Found: C, 65.24; H, 6.88; N, 13.76

Example 4

N-[4-[(Aminothioxomethyl)hydrazono]-4-phenylbutyl]-N-(1-methylethyl)cyclohexanecarboxamide In the manner as described in Example 1 and substituting cyclohexanecarbonyl chloride for acetyl chloride in step c, the title compound was obtained (1.48 g, 40%) as a white solid, mp 112–114° C.

Elemental Analysis for $C_{21}H_{32}N_4OS$.0.07 $C_6H_{14}$.0.22 $C_4H_8O_2$ Calc'd: C, 64.70; H, 8.46; N, 13.53 Found: C, 64.72; H, 8.63; N, 13.10

Example 5

N-[4-[(Aminothioxomethyl)hydrazono]-4-phenylbutyl]cyclohexanecarboxamide

In the same manner as described in Example 2 and substituting cyclohexanecarbonyl chloride for acetyl chloride in step c, the title compound was obtained (2.19 g, 51%) as a light yellow solid after recrystallization from isopropyl alcohol, mp 158–159° C.

Elemental Analysis for $C_{18}H_{26}N_4OS$ Calc'd: C, 62.40; H, 7.56; N, 16.17 Found: C, 62.37; H, 7.39; N, 15.87

Example 6

N-[4-[(Aminothioxomethyl)hydrazono]-4-phenylbutyl]hexanamide

In the same manner as described in Example 2 and substituting hexanoyl chloride for acetyl chloride in step c, the title compound was obtained (3.48 g, 53%) as a light yellow solid, mp 125–127° C.

Elemental Analysis for $C_{17}H_{26}N_4OS$ Calc'd: C, 61.05; H, 7.84; N, 16.75 Found: C, 61.10; H, 7.59; N, 16.89

Example 7

N-[4-[[(Methylamino)thioxomethyl]hydrazono]-4-phenylbutyl]benzamide

In the same manner as described in Example 2 and substituting benzoyl chloride for acetyl chloride in step c, the title compound was obtained (1.47 g, 64%) as a white solid, mp 114–118° C.

Elemental Analysis for $C_{19}H_{22}N_4OS$.0.5 $H_2O$ Calc'd: C, 62.79; H, 6.38; N, 15.41 Found: C, 62.64; H, 6.39; N, 15.10

Example 8

2-[2-(Benzylcarbonylamino)-1-phenyl-butylidene]-hydrazinecarbothioamide

In the same manner as described in Example 2 and substituting phenylacetyl chloride for acetyl chloride in step c, the title compound was obtained (2.52 g, 62%) as a white solid after recrystallization from isopropyl alcohol, mp 121–124° C.

Elemental Analysis for $C_{19}H_{22}N_4OS$ Calc'd: C, 64.38; H, 6.26; N, 15.81 Found: C, 64.33; H, 6.23; N, 15.71

Example 9

N-[4-[(Aminothioxomethyl)hydrazono]-4-(4-fluorophenyl)butyl]-N-(1-methylethyl)acetamide In the same manner as described in Example 1 and substituting γ-(4-fluorophenyl)-γ-butyrolactone for γ-phenyl-γ-butyrolactone in step 1, the title compound was obtained (2.10 g, 49%) as a white solid after recrystallization from isopropyl alcohol, mp 155–157° C.

Elemental Analysis for $C_{16}H_{23}FN_4OS \cdot 0.36\ C_3H_8O$ Calc'd: C, 56.97; H, 7.24; N, 15.56 Found: C, 56.52; H, 7.18; N, 15.08

PHARMACOLOGY

In Vivo Assay: Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Procedure No. 352, modified for use with ninety-six well microtiter plates. After reconstitution with water the reagent contains 300 U/I cholesterol oxidase, 100 U/I horse radish peroxidase, 0.3 mmoles/I 4-aminoantipyrine and 30.0 mmoles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., J. Lipid Res., 32 (1991) 859–866. 25 μl of serum is injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the per cent of total absorbance. HDL cholesterol concentration, in serum, is calculated as the per cent of total cholesterol as determined by FPLC multiplied by the total serum cholesterol concentration.

TABLE I

| Cholesterol Fed Rat | |
|---|---|
| Example | % Increase in HDL (Dose) |
| Example 1 | 87% (50 mg/kg) |
| Example 2 | 81% (33 mg/kg) |
| Example 3 | 26.1% (50 mg/kg) |
| Example 4 | 59.7% (50 mg/kg) |
| Example 5 | 58.1% (50 mg/kg) |
| Example 6 | 56.7% (50 mg/kg) |
| Example 7 | 27.2% (50 mg/kg) |
| Example 8 | 44.5% (100 mg/kg) |
| Example 9 | 80.2% (50 mg/kg) |

PHARMACEUTICAL COMPOSITION

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties In suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilize by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from high density lipoprotein insufficiency must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral or parenteral administration will be determined by the administering physician based on experience with the individual subject treated and standard medical principles.

Preferably the pharmaceutical composition is in unit dosage form, e.g., as tablets or capsules. In such form, the composition is sub-divided in unit doses containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A compound of the formula:

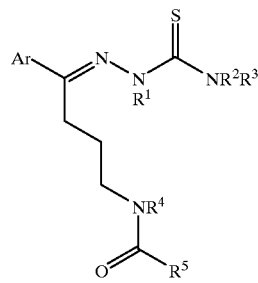

wherein:
R$^1$, R$^2$, and R$^3$ are independently hydrogen, C$_1$–C$_6$ alkyl or —(CH$_2$)$_{0-6}$Ph where Ph is phenyl is optionally substituted by halogen, cyano, nitro, C$_1$–C$_6$ alkyl, C$_1$–C$_6$ alkoxy, trifluoromethyl, C$_1$–C$_6$ alkoxycarbonyl, —CO$_2$H or OH;

R$^4$ is hydrogen or C$_1$–C$_6$ alkyl;

R$^5$ is hydrogen, C$_1$–C$_6$ alkyl, C$_3$–C$_8$ cycloalkyl, or —(CH$_2$)$_{0-6}$Ar$^1$ where Ar$^1$ is phenyl, naphthyl, furanyl, pyridinyl or thienyl and Ar$^1$ is optionally subsituted by halogen, cyano, nitro, C$_1$–C$_6$ alkyl, phenyl, C$_1$–C$_6$ alkoxy, phenoxy, trifluoromethyl, C$_1$–C$_6$ alkoxycarbonyl, —CO$_2$H or OH; and Ar is phenyl, naphthyl, furanyl, pyridinyl or thienyl where Ar is optionally substituted by halogen, cyano, nitro, C$_1$–C$_6$alkyl, phenyl, C$_1$–C$_6$alkoxy, phenoxy, trifluoromethyl, C$_1$–C$_6$ alkoxycarbonyl, —CO$_2$H or OH.

2. A compound according to claim 1 which is N-[4-[(aminothioxomethyl)hydrazono]-4-phenylbutyl]-N-(1-methylethyl)acetamide.

3. A compound according to claim 1 which is N-[4-[(aminothioxomethyl)hydrazono]-4-phenylbutyl]acetamide.

4. A compound according to claim 1 which is N-[4-[(aminothioxomethyl)hydrazono]-4-phenylbutyl]-N-(1-methylethyl)benzamide.

5. A compound according to claim 1 which is N-[4-[(aminothioxomethyl)hydrazono]-4-phenylbutyl]-N-(1-methylethyl)cyclohexanecarboxamide.

6. A compound according to claim 1 which is N-[4-[(aminothioxomethyl)hydrazono]-4-phenylbutyl]cyclohexanecarboxamide.

7. A compound according to claim 1 which is N-[4-[(aminothioxomethyl)hydrazono]-4-phenylbutyl]hexanamide.

8. A compound according to claim 1 which is N-[4-[[(methylamino)thioxomethyl]hydrazono]-4-phenylbutyl]benzamide.

9. A compound according to claim 1 which is 2-[2-(benzylcarbonylamino)-1-phenyl-butylidene]-hydrazinecarbothioamide.

10. A compound according to claim 1 which is N-[4-[(aminothioxomethyl)hydrazono]-4-(4-fluorophenyl)butyl]-N-(1-methylethyl)acetamide.

11. A method for increasing HDL in the blood which comprises administration to a mammal having atherosclerosis a therapeutically effective amount of a compound of the formula

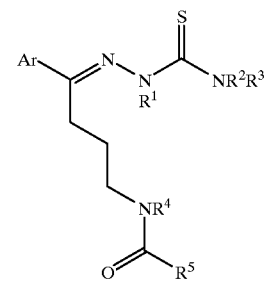

wherein:
R$^1$, R$^2$, and R$^3$ are independently hydrogen, C$_1$–C$_6$ alkyl or —(CH$_2$)$_{0-6}$Ph where Ph is phenyl is optionally substituted by halogen, cyano, nitro, C$_1$–C$_6$ alkyl, C$_1$–C$_6$ alkoxy, trifluoromethyl, C$_1$–C$_6$ alkoxycarbonyl, —CO$_2$H or OH;

R$^4$ is hydrogen or C$_1$–C$_6$ alkyl;

R$^5$ is hydrogen, C$_1$–C$_6$ alkyl, C$_3$–C$_8$ cycloalkyl, or —(CH$_2$)$_{0-6}$Ar$^1$ where Ar$^1$ is phenyl, naphthyl, furanyl, pyridinyl or thienyl and Ar$^1$ is optionally subsituted by halogen, cyano, nitro, C$_1$–C$_6$ alkyl, phenyl, C$_1$–C$_6$ alkoxy, phenoxy, trifluoromethyl, C$_1$–C$_6$ alkoxycarbonyl, —CO$_2$H or OH;

Ar is phenyl, naphthyl, furanyl, pyridinyl or thienyl where Ar is optionally substituted by halogen, cyano, nitro, C$_1$–C$_6$alkyl, phenyl, C$_1$–C$_6$alkoxy, phenoxy, trifluoromethyl, C$_1$–C$_6$ alkoxycarbonyl, —CO$_2$H or OH.

12. The method according to claim 11 wherein the therapeutically effective compound used is N-[4-[(aminothioxomethyl)hydrazono]-4-phenylbutyl]-N-(1-methylethyl)acetamide.

13. The method according to claim 11 wherein the therapeutically effective compound used is N-[4-[(aminothioxomethyl)hydrazono]-4-phenylbutyl]acetamide.

14. The method according to claim 11 wherein the therapeutically effective compound used is N-[4-[(aminothioxomethyl)hydrazono]-4-phenylbutyl]-N-(1-methylethyl)benzamide.

15. The method according to claim 11 wherein the therapeutically effective compound used is N-[4-[(aminothioxomethyl)hydrazono]-4-phenylbutyl]-N-(1-methylethyl)cyclohexanecarboxamide.

16. The method according to claim 11 wherein the therapeutically effective compound used is N-[4-[(aminothioxomethyl)hydrazono]-4-phenylbutyl]cyclohexanecarboxamide.

17. The method according to claim 11 wherein the therapeutically effective compound used is N-[4-[(aminothioxomethyl)hydrazono]-4-phenylbutyl]hexanamide.

18. The method according to claim 11 wherein the therapeutically effective compound used is N-[4-[[(methylamino)thioxomethyl]hydrazono]-4-phenylbutyl]benzamide.

19. The method according to claim 11 wherein the therapeutically effective compound used is 2-[2-(benzylcarbonylamino)-1-phenyl-butylidene]hydrazinecarbothioamide.

20. The method according to claim 11 wherein the therapeutically effective compound used is N-[4-[(aminothioxomethyl)hydrazono]-4-(4-fluorophenyl)butyl]-N-(1-methylethyl)acetamide.

21. A pharmaceutical composition comprising a pharmaceutically acceptable carrier and a compound of the formula

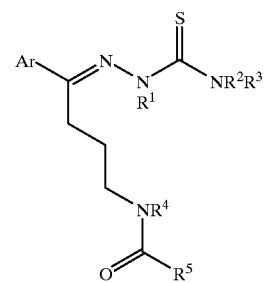

wherein:

$R^1$, $R^2$, and $R^3$ are independently hydrogen, $C_1$–$C_6$ alkyl or —$(CH_2)_{0-6}$Ph where Ph is phenyl is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ is hydrogen or $C_1$–$C_6$ alkyl;

$R^5$ is hydrogen, $C_1$–$C_6$ alkyl, $C_3$–$C_8$ cycloalkyl, or —$(CH_2)_{0-6}Ar^1$ where $Ar^1$ is phenyl, naphthyl, furanyl, pyridinyl or thienyl and $Ar^1$ is optionally subsituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl, naphthyl, furanyl, pyridinyl or thienyl where Ar is optionally substituted by halogen, cyano, nitro, $C_1$–$C_6$alkyl, phenyl, $C_1$–$C_6$alkoxy, phenoxy, trifluoromethyl, $C_1$–$C_6$ alkoxycarbonyl, —$CO_2H$ or OH.

* * * * *